US008172791B2

(12) United States Patent
Callanan et al.

(10) Patent No.: US 8,172,791 B2
(45) Date of Patent: May 8, 2012

(54) BREAST MILK COLLECTION AND STORAGE DEVICE

(76) Inventors: Renee Jetton Callanan, Sheridan, OR (US); Helen J. Anderson, McMinnville, OR (US)

( * ) Notice: Subject to any disclaimer, the term of this patent is extended or adjusted under 35 U.S.C. 154(b) by 0 days.

(21) Appl. No.: 12/781,667

(22) Filed: May 17, 2010

(65) Prior Publication Data

US 2010/0228208 A1 Sep. 9, 2010

Related U.S. Application Data

(63) Continuation-in-part of application No. 11/956,765, filed on Dec. 14, 2007, now abandoned.

(51) Int. Cl.
*A61M 1/06* (2006.01)
(52) U.S. Cl. .......................................................... 604/74
(58) Field of Classification Search ...................... 604/74
See application file for complete search history.

(56) References Cited

U.S. PATENT DOCUMENTS

| 4,501,585 A | 2/1985 | Friedman |
| 5,358,476 A | 10/1994 | Wilson |
| 5,385,251 A | 1/1995 | Dunn |
| 5,531,231 A | 7/1996 | Morrissey et al. |
| 5,732,714 A | 3/1998 | Morrissey et al. |
| 6,247,996 B1 | 6/2001 | Fields |
| 6,328,082 B1 | 12/2001 | Lafond |
| 6,440,100 B1 * | 8/2002 | Prentiss ........................ 604/74 |
| 6,551,639 B1 | 4/2003 | Nye et al. |
| 6,749,582 B2 | 6/2004 | Britto et al. |
| 6,884,229 B2 | 4/2005 | Renz |
| 6,910,594 B2 | 6/2005 | Foley et al. |
| 7,223,255 B2 | 5/2007 | Myers et al. |
| 2003/0191433 A1 * | 10/2003 | Prentiss ........................ 604/74 |
| 2008/0262419 A1 * | 10/2008 | Rollin ............................ 604/74 |

* cited by examiner

*Primary Examiner* — Nicholas Lucchesi
*Assistant Examiner* — Jason Flick
(74) *Attorney, Agent, or Firm* — Peter A. Haas Esquire LLC

(57) ABSTRACT

In a preferred embodiment, the present invention includes a breast milk collection and storage device that contours to the natural form of a female human breast and consists of an outer layer, an inner layer and a sterile collection bag. Designed to fit under any standard brassiere, the device provides an opening to be comfortably worn around the nipple. The opening directs mild to the sterile collection bag and further provides a sealing means for coupling to a cap or other closure device when not being worn.

5 Claims, 11 Drawing Sheets

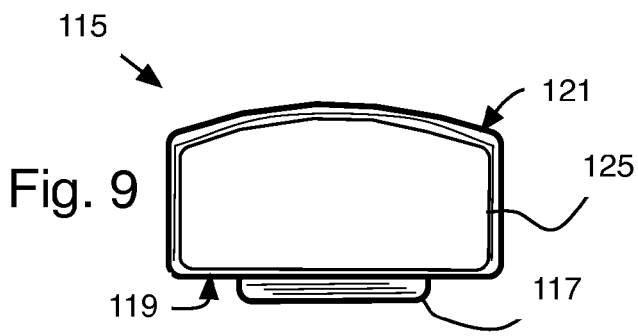
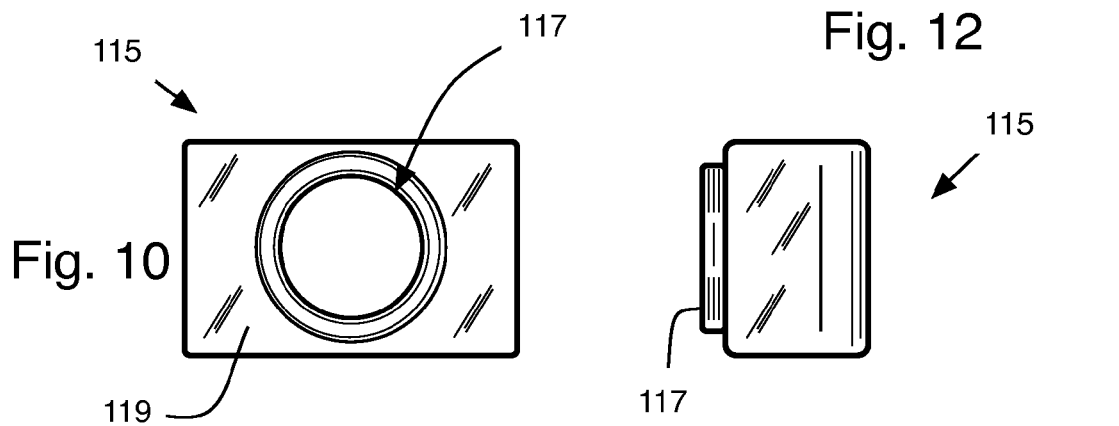
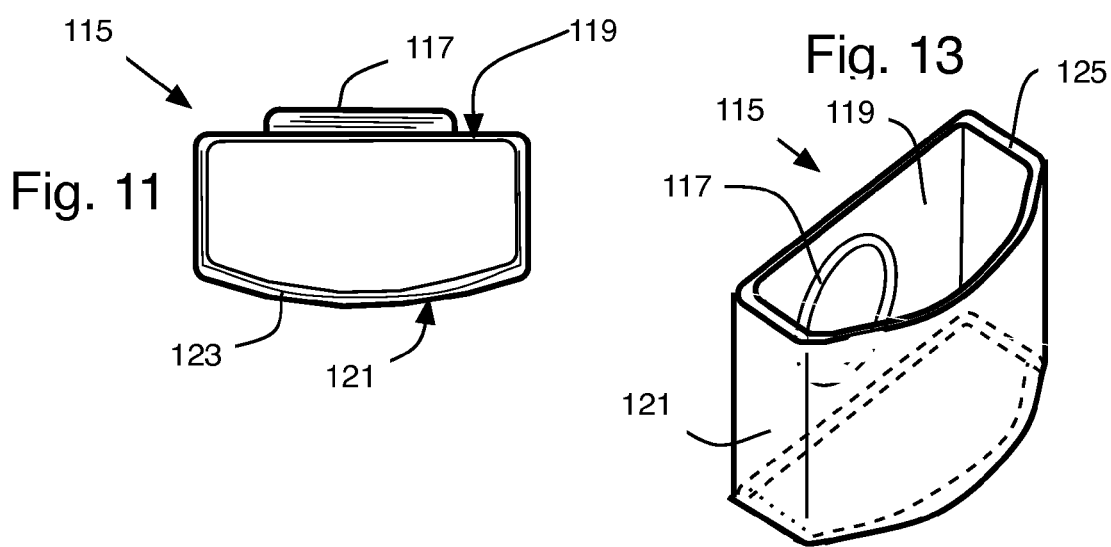

BREAST MILK COLLECTION AND STORAGE DEVICE

PRIORITY CLAIM

The present application is a continuation in part of earlier filed, non-provisional and co-pending U.S. patent application Ser. No. 11/956,765 filed on 14 Dec. 2007 by the same inventors. The present application is based on and claims priority from this application pursuant to 35 USC 120, the disclosure of which is hereby expressly incorporated herein by reference.

BACKGROUND

The present invention relates to concealable, breast milk collection and storage devices for lactating mothers.

Natural breastfeeding infants, widely accepted as the best way to nurture an infant, often causes practical limitations particularly to working mothers or otherwise active mothers who are often in public spaces and are unable to immediately locate a private or discrete location where they can comfortably feed their infant or collect the breast milk for a later use. Recognizing this problem, the prior art presents many varied attempts to provide devices that enable a lactating mother to collect or prevent lactation.

Broadly, the state-of-the-art categorizes into three classifications including concealed devices for collection or storage, non-concealable pumping and storing apparatuses, and concealed lactation prevention devices.

Representative of the first class of concealed devices, devices worn similar to undergarments, includes the concealed apparatus for hands free breast milk pumping and storage of Prentiss disclosed in U.S. Pat. No. 6,440,100 issued on 27 Aug. 2002. Prentiss further teaches an external conduit for transferring expelled breast milk from the nipple to a remote reservoir located outside the brassiere. The Prentiss apparatus includes a low-profile nipple cap held in place beneath a support brassier. This apparatus permits concealed, hands-free breast pumping in a public environment without any remarkable change in the user's visible appearance. Milk is expressed from the breasts through the nipple cap, which links to a remote reservoir via a milk storage conduit. A vacuum is applied to the storage reservoir by an electronic or manual pump. One limitation of the Prentiss apparatus includes the necessity of an external or remote reservoir bag. Further, the Prentiss apparatus requires a remote or external pump device to extract the milk. The additional, remote or external pump and bag destroy the privacy or operation discretion desired by many mothers, requiring them to find a more private or less-public venue to attend to the collection of breast milk. Thus, there remains a need for a device that operates when completely concealed, and such a device should further eliminate the extra equipment as taught by Prentiss.

The second category, non-concealable pumping and storing apparatuses, is well represented in the prior art and typically comprise a funnel-like device adapted to fit over the nipple and a portion of a female breast, a conduit member linking the funnel and directing milk to a collection device. Typically, the collection device is a bag. A representative example of the prior art includes a breast milk pump support harness disclosed by Fields in U.S. Pat. No. 6,247,996 issued on 19 Jun. 2001. Fields describes a support harness to be worn by a nursing mother that includes two detachable collection bottle support assemblies and a brassiere assembly. Examples of bags and collection funnels include a disposable sterile bag disclosed by Lafond in U.S. Pat. No. 6,328,082 issued on 11 Dec. 2001. Lafond describes a disposable plastic bag with a liquid receiving chamber having a tear-off strip and closure member. Limitations of this classification of these non-concealable pumping and storing apparatuses include their inability to be concealed beneath outer garments, require remote pumping devices, and are inoperable to discretely collect breast milk. Thus, there remains a need for a collection system that can easily be worn under outer garments, yet retain a normal appearance for the user when worn. Such a device should include a collection means that does not require a remote or external pump apparatus.

Attempts to both conceal and prevent lactation include devices described by Morrissey et al. in U.S. Pat. No. 5,531,231 issued on 2 Jul. 1996 and in U.S. Pat. No. 5,732,714 issued on 31 Mar. 1998 include an apparatus having an outer surface and an inner surface shaped to conform substantially to a human female breast and having a protrusion with a substantially flat, nipple-contacting surface which extends away from the support and positions to align substantially with and contact a nipple, and thus preventing lactation when placed over the breast. The Morrissey device, however, does not teach or disclose any means for collecting breast milk, and attempts to prevent lactation. This device does not adequately address the need for a concealed collection device.

The prior-art is silent on a device or method to collect a small amount (up to about four ounces) of milk that leaks from the non-nursing side during breastfeeding. In fact, the prior art teaches that the non-nursing side be blocked, or that milk be absorbed (i.e., nursing pads), or pumped. Thus, there remains a need for a concealable device that collects milk that leaks from the non-nursing side during breastfeeding and such a collection device should be concealable and not require external storage container or pump apparatus. To aid concealment under a brassiere, such a device should contour to the natural shape of the female breast, and to further enhance concealment and comfort during use, such a device should be completely encapsulated by a single cup of the brassiere. Further, the device should be easy to wear with a supportive brassiere, provide a normal appearance when viewed under clothing, provide a means for collecting milk that can be reused, easily cleaned, and seal to retain the milk for later use, while simultaneously enabling a mother to breast feed from one breast. A much simpler device, one that does not require conduits to large-volume storage bags, does not require external pumping, does not require concealment of external apparatus, us very much needed.

SUMMARY OF THE INVENTION

The prior art can be summarized into one of two general teaching: provide absorbing means or provide pumping means for collecting a large volume of mother's milk for future use. In contrast, the present invention does not absorb milk, which would make its re-use impossible, nor does the present invention provide means for storing a large volume of milk. Rather, the present invention enables a mother to breast feed an infant from one breast, while collecting a small volume of milk that naturally lets-down from the non-nursing breast. The present invention is, therefore, much simpler to make, easier to use, and easy to conceal. The present invention solves problems not contemplated in the prior-art: Namely, how to collect small amounts of milk from then non-feeding side during breast-feeding. The present invention enables and allows a nursing mother to breastfeed anywhere without worrying about embarrassing leaks or uncomfortable nursing pads. Slim and portable, and therefore easy to conceal, it encourages nursing moms to collect what would (by the prior-art teaching) be wasted milk.

Nursing pads of the prior art absorb milk from then non-feeding breast, this milk cannot be used and therefore is wasted. The present invention, in contrast, provides a means for collecting this milk from the non-feeding breast during feeding using the other breast and the present invention does not require any pumps.

The present invention overcomes the aforementioned limitations of the prior art and provides a concealable device for collecting breast milk without requiring use of a remote or external pump device. Further, the present invention, contrary to the teaching of the prior art, does not include a conduit tube for extracting expelled breast milk from the nipple region to a remote reservoir. Instead, the present invention accumulates let-down milk in a reservoir that is immediately adjacent to the nipple, the reservoir contours to the breast and locates and is otherwise completely encapsulated under the brassiere. This vastly improves over the prior art, which teaches that the expelled milk be transferred from a position adjacent to the nipple to a remote reservoir that locates outside the brassiere and is not adjacent to the breast and completely encapsulated by the brassiere.

Prentiss contemplates pumping the contents of one or both breasts for collection and later use (i.e. bottle feeding of an infant). To accommodate this larger volume of fluid, a large-volume storage bag 10 is required. This storage bag—because of its volume—must locate away from the breast. This in turn requires conduits 14 to carry fluid from the nipple to the storage bag. Further, Prentiss teaches a pump mechanism to draw (with suction) milk from the breast into the storage bag—this requires additional complexity and components not required in Applicant's claimed invention.

In contrast with the large, remote storage container and associated conduits of Prentiss, the present invention consists of a collection and storage device adapted to fit over a human female nipple and portion of a female breast, and preferably under a supportive brassiere. The entire storage bag fits under the brassiere and adjacent to the breast because the volume collected is significantly less than the volume contemplated by Prentiss. Further, the applicant's device intends to provide a natural shape and appearance when worn in contact with skin under apparel.

More specifically, the present invention's entire storage volume resides between the inner and outer contours and is designed to keep the lactating milk stored under a supporting brassiere. The applicant's device is meant to be a discrete collection tool for naturally lactating breasts and is not designed to "pump" milk from the breast for later use. Rather, the applicant's device replaces the prior-art absorbing pads. The prior-art pads are similarly designed for discrete use to prevent naturally lactating milk from "leaking" through a mother's clothing, which may prove to be embarrassing, especially in a male-dominated work world. However, the present invention recognizes that breast-milk is a valuable (to the infant's health) product that should not be wasted (as would be with the absorbing pads of the prior art). Instead, applicant's device enables the collection of the small (approximately 2 ounces) of breast milk.

Because applicant's device is not pumping a larger volume of milk (as taught by Prentiss) for bottle-feeding, the retention volume of the Applicant's device is much smaller than the pumping devices exemplified by Prentiss '100. Further, as Applicant's device is not pumping milk it requires less structure and can allow collection under the brassiere and allow the wearer to maintain a more natural profile.

The present invention overcomes many of the limitations the cited reference as the Applicant's device requires less components, is less complex and therefore less costly to produce, resulting in a more economical product. Further, applicant's device solves a problem not contemplated by Prentiss, namely the collection of trace amounts of lactating milk between feedings In a preferred embodiment, the present invention includes a breast milk collection and storage device that contours to the natural form of a female human breast and consists of an outer layer, an inner layer and a sterile collection bag. Designed to fit under any standard brassiere, the device provides an opening to be comfortably worn around the nipple. The opening directs mild to the sterile collection bag and further provides a sealing means for coupling to a cap or other closure device when not being worn. The present invention is designed to be worn on the non-nursing side during breastfeeding and is designed to capture up to about 4-oz. of milk that leaks from the non-nursing side during breastfeeding. Traditionally, this leaked milk was absorbed in a nursing pad or otherwise wasted.

Other advantages and features of the present invention include a slim design making use discrete, easy to use features that encourage capturing, saving and using milk that would otherwise be wasted, comfortable shape and soft materials, eliminates disposable nursing products such as absorbing pads and plastic bags/liners, use of an FDA-approved material that is BHT and phthalate-free and is independently tested to ensure zero chemical leaching, durable, recyclable, stylish and sturdy, includes a protective case for storage and transport, economical to use (simply wash with hot soapy water, rinse, and allow to dry thoroughly—reuse as many times as needed), saves money, and is environmentally conscious, for example. Further, the present invention works with existing milk storage bags, enabling the nursing mom to transfer the milk collected from the non-nursing side while breastfeeding, to use later in a bottle.

Further, the protective travel case also includes a feature that enables the collection device to stand upright.

DRAWING

FIG. 9 is a top view of a detachable rim member of the embodiment of FIG. 8.

FIG. 10 is a back view of the detachable rim member of FIG. 9.

FIG. 11 is a bottom view of the detachable rim member of FIG. 9.

FIG. 12 is a left-side view of the detachable rim member of FIG. 9.

FIG. 13 is an offset frontal view of the detachable rim member of FIG. 9.

DESCRIPTION OF THE INVENTION

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

Figure 1:
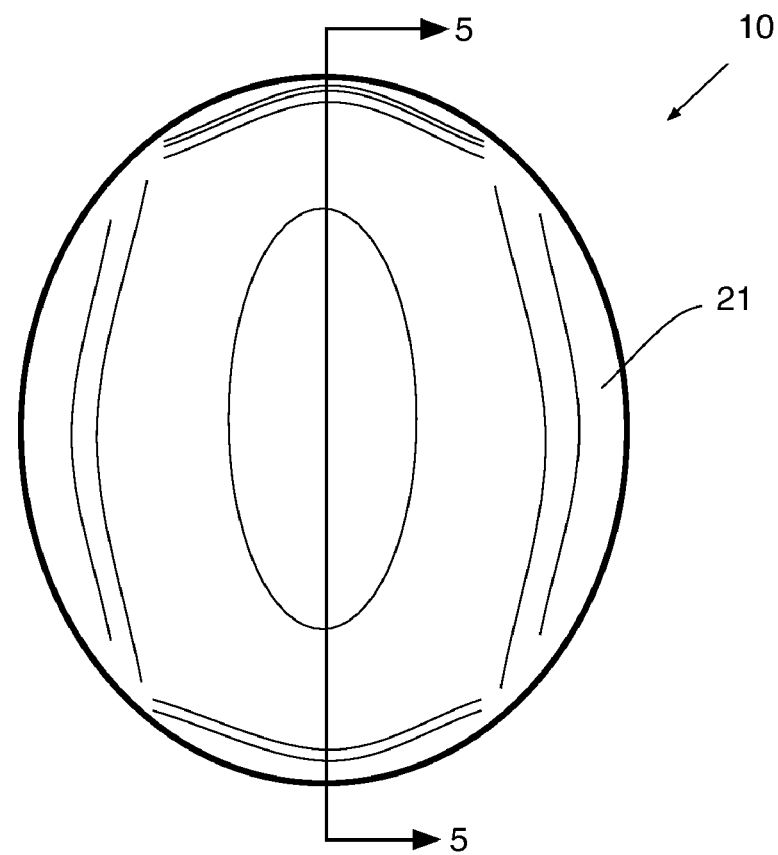
FIG. 1 is a front view of a first preferred embodiment of the present invention.
Figure 2:
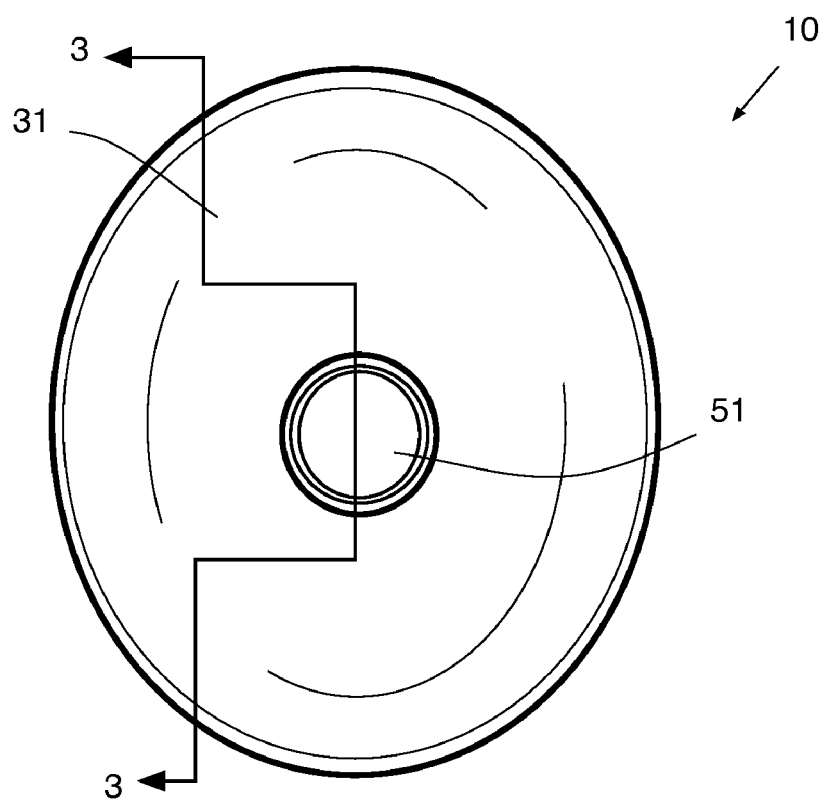
FIG. 2 is a back view of the embodiment of FIG. 1.
Figure 4:
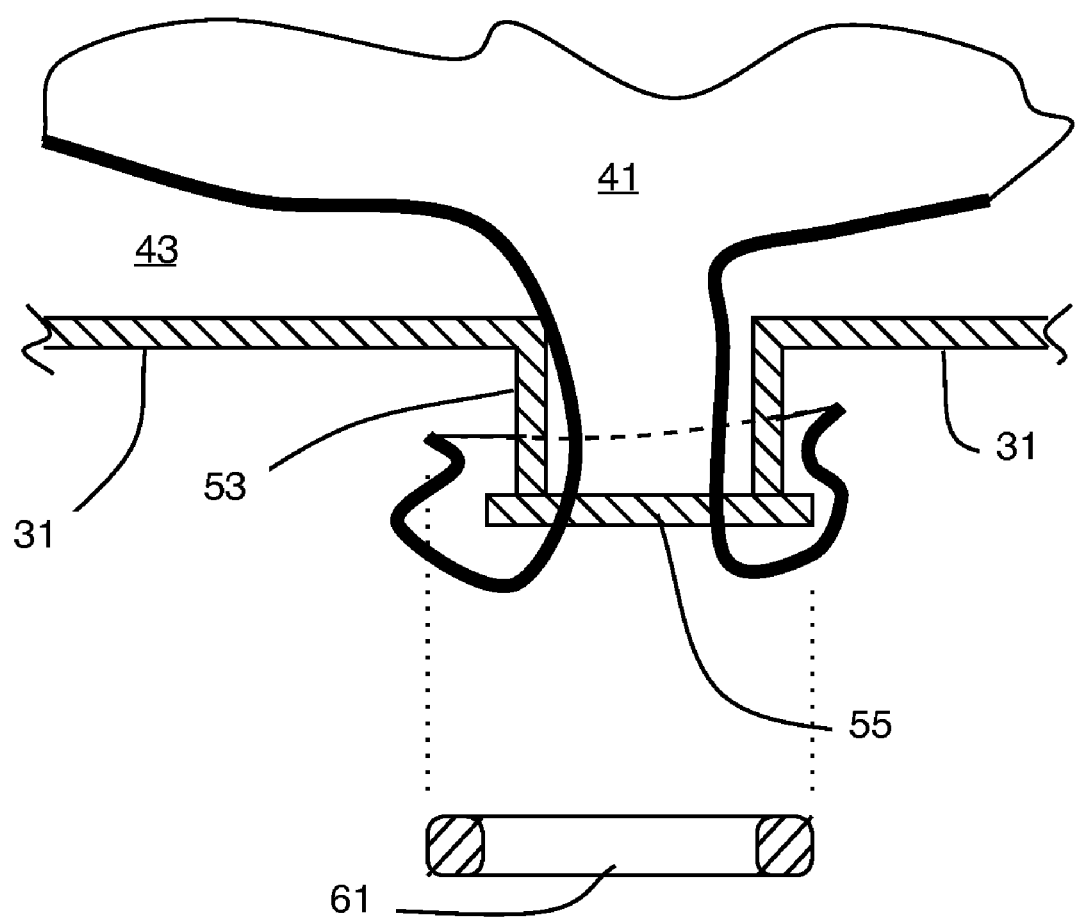
FIG. 4 is a partial cross-sectional side view detailing an opening according to a second preferred embodiment of the present invention.

FIGS. 1, 2 and 4 show a first preferred embodiment of the present invention, which consists of a breast milk collection and storage device 10. The collection and storage device adapts to fit over a human female nipple and portion of a female breast, and preferably under a supportive brassiere to provide a natural shape and appearance when worn in contact with skin under apparel. The device 10 includes an outer layer 21 having a first contour. The first contour emulates the curve and contour of a human female breast. For example the outer layer consists of a generally convex elliptical form when viewed from above and measures about a 6-inch diameter on the minor axis and about an 8-inch diameter on the major axis and consists of a relatively soft and resiliently deformable material such as a silicon-type material as would be appreciated by those with skill in this art. One suitable material for the inner and outer layers includes the brand-name STERalloy FDG available from www.hapcoweb.com, which is a liquid molding polymer alloy that has been specifically designed for food and drug applications.

The device 10 further consists of an inner layer 31 having a second contour. The second contour also emulates the curve and contour of a human female breast, but is sized to create a cavity when coupled to the outer layer. For example, the inner layer 31 consists of a generally concave circular form when viewed from above and measures about 6-inches in diameter.

Figure 3:
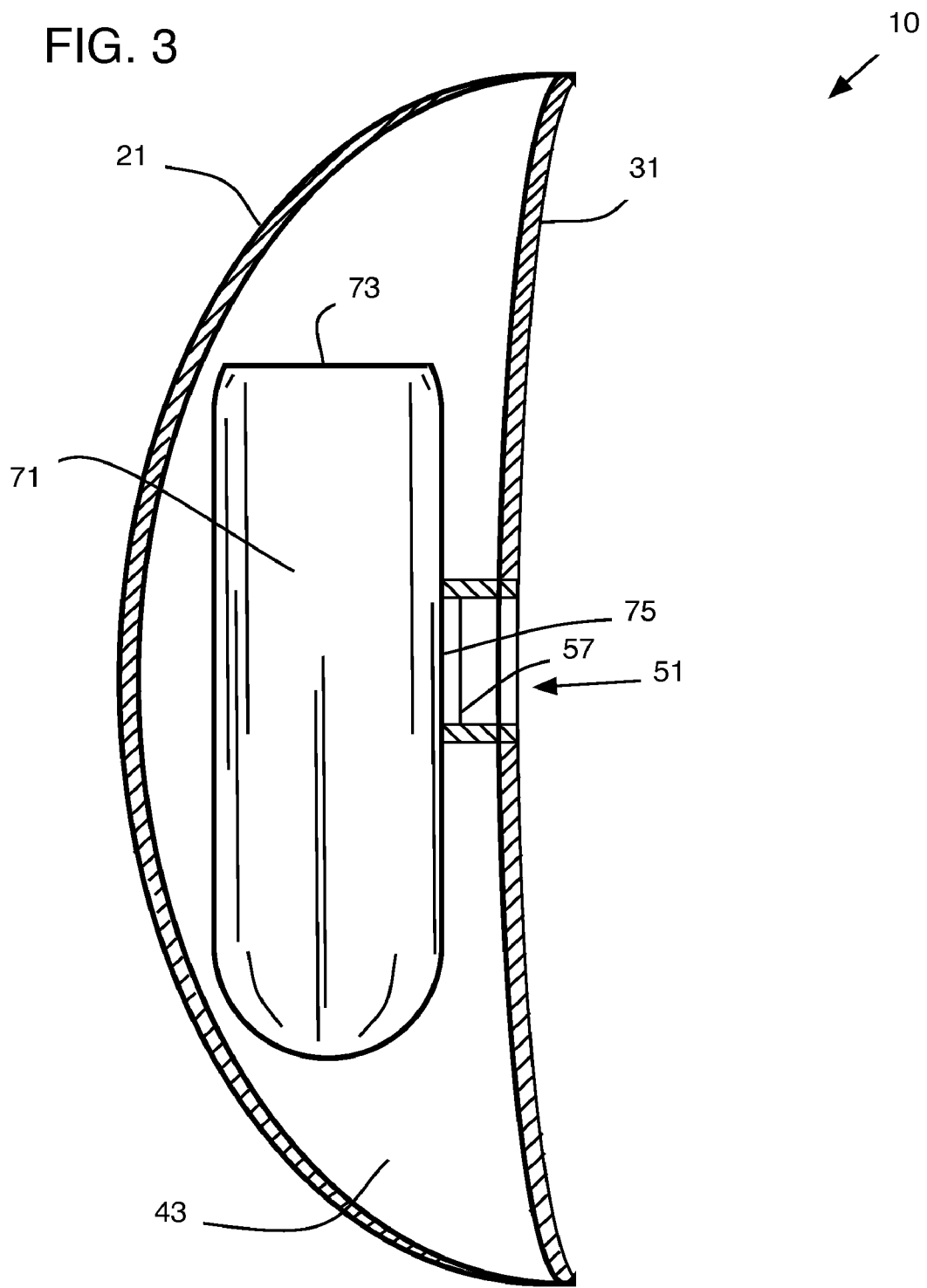
FIG. 3 is a cross-sectional side view along the line 3-3 of FIG. 2.

The outer layer 21 couples to the inner layer 31 along two separate portions of a common boundary between the two layers. The two layers align their respective concavity in the same direction to form a cavity 43, a volume that appears generally crescent-shaped when viewed in profile. FIG. 3 clearly illustrates the crescent-shaped cavity 43 with respect to the inner layer 31 and outer layer 21. As would be understood in this art, a portion of the boundary between the outer layer and inner layer aligns coincident with each other, and serves as a join-edge during the fabrication process. This join-edge may readily be adhered by using a suitable adhesive or molded in the desired configuration. Also, a portion of the boundary between the inner and outer layers will remain open and not coupled together. This opening lends itself readily to aiding the insertion and retraction of the collection bag 41.

In certain alternative preferred embodiments, the join-edge consists of a portion of the common boundary between the inner and outer layers and acts as a hinge. In this way the inner layer may nest in close proximity to the outer layer for storage or when worn. Thus, as breast milk collects in the collection bag, the outer layer may expand outward with respect to the wearer and the cavity 43 would vary in volume as the outer layer adjusts to changes in the volume of milk collected.

Facilitating collection of breast milk, the device 10 further includes a nipple-receiving opening 51 disposed on the inner layer 31. The opening 51 adapts to enable the human female nipple to insert therethrough and create a fluid conduit from the inner layer to the cavity 43 or directly to a collection bag 41.

FIG. 4 more clearly illustrates a suitable collection bag 41, which adapts to arrange within the cavity 43 formed between the inner and outer layers. The cavity may include several openings, as previously discussed. The collection bag 41—any number of disposable plastic and sterile bags adapted for use to collect breast milk, as would be well understood in this art, can adapt for use as the collection bag of the present invention—arranges in the cavity and presents an opening to align with the nipple-receiving opening 51 so that breast milk can flow from the lactating mother's breast into the collection bag. The collection bag, accordingly, selectively couples to the inner layer, or to the opening 51.

FIG. 4 also shows one alternative preferred embodiment of a suitable nipple-receiving opening 51. This opening is circular (as FIG. 2 illustrates) in cross section—although other shapes can work equally well including a slit, oval, or rectangle, for example. In this embodiment, the opening 51 includes a shoulder 53 protruding from the surface of the inner layer 31 at a first shoulder end. A circular flange 55 forms at an oppositely disposed second shoulder end. The flange 55 cooperates with the retaining member 61, for example an elastically deformable member such as an O-ring or rubber band, to retain an open end of the collection bag 41 in position to enable fluid flow into the collection bag.

The retention member 61, in another preferred embodiment, removes from the nipple-receiving opening 51, enabling the now-full collection bag to be removed from the inner layer and outer layer assembly. And, the retention member 61 now serves as a sealing member to close the now-full collection bag to prevent leakage.

FIG. 3 shows another preferred embodiment of a breast milk collection device 10 having a rigid inner cup 71 formed or molded from a polyproponal or other similar plastic material. The inner cup includes an open top portion 73 and vertical sidewalls and a bottom cooperating to form a compartment 77. An access port 75 disposed on one vertical sidewall aligns with the fluid conduit 57 portion of the inner layer 31 to provide a fluid-flow path from the female nipple to the collection cup 71.

Figure 5:
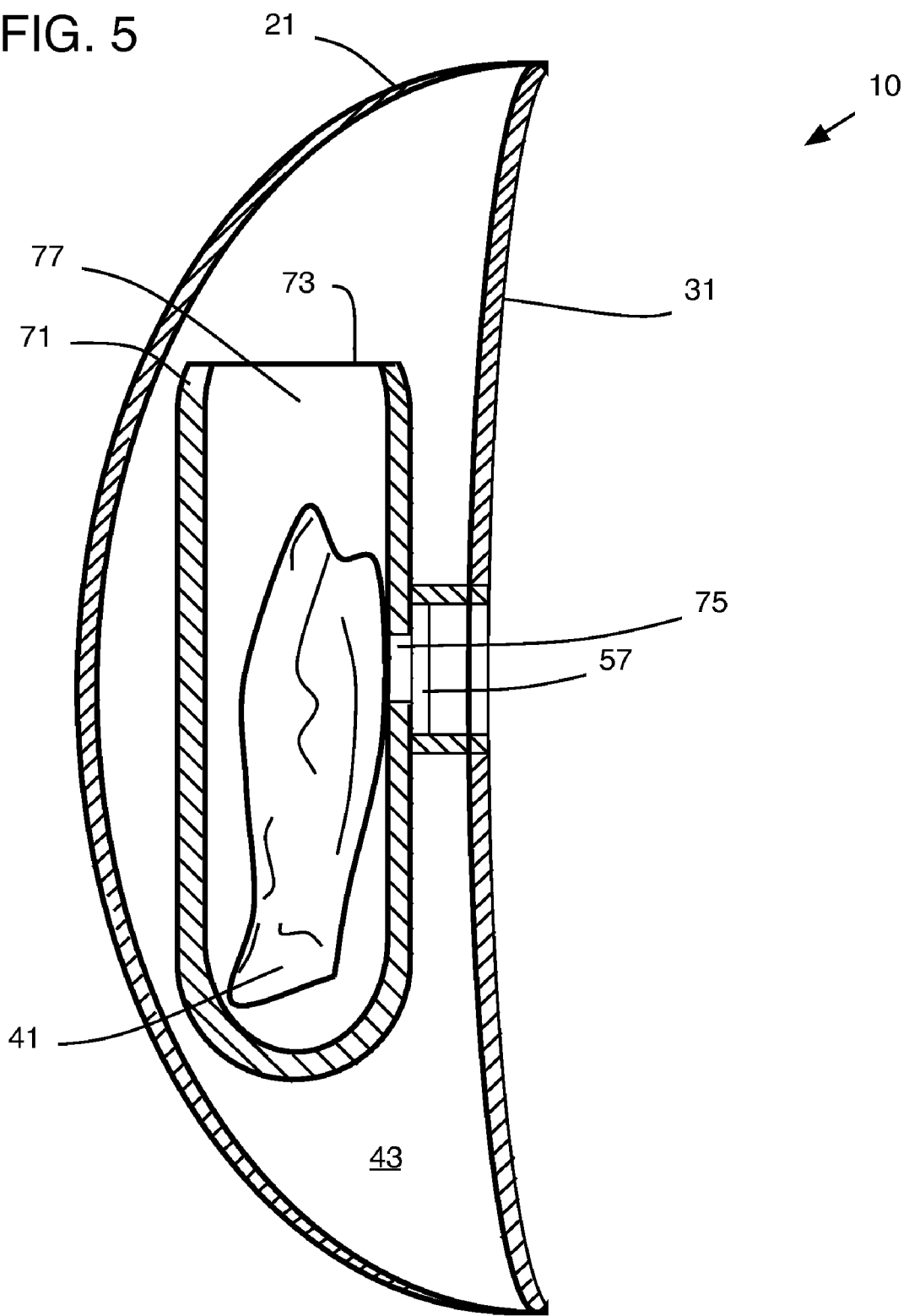
FIG. 5 is a cross-sectional side view along the line 5-5 of FIG. 1.
Figure 7:
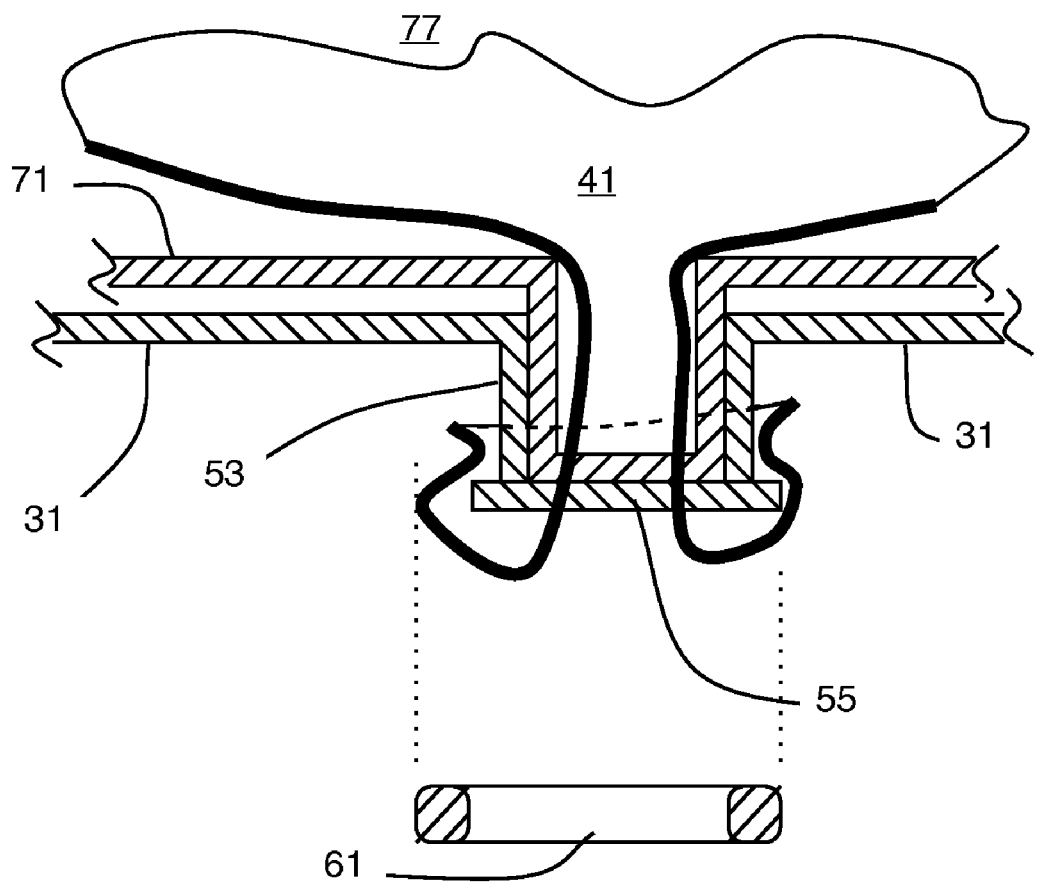
FIG. 7 is a partial cross-sectional side view detailing an opening according to another preferred embodiment of the present invention.

FIG. 5 shows the collection cup 71 being used with a bag liner 41, which can easily be inserted through the open top 73. FIG. 7 further details a possible arrangement of components relative to the inner layer 31. An o-ring type sealing member 61 or rubber band inserts over a flange 55 onto a neck 53 of the fluid conduit 57, which provides a fluid passage to the inner compartment 77 of the cup 71 or to a bag liner 41 inserted in the same inner compartment 77.

Figure 6:
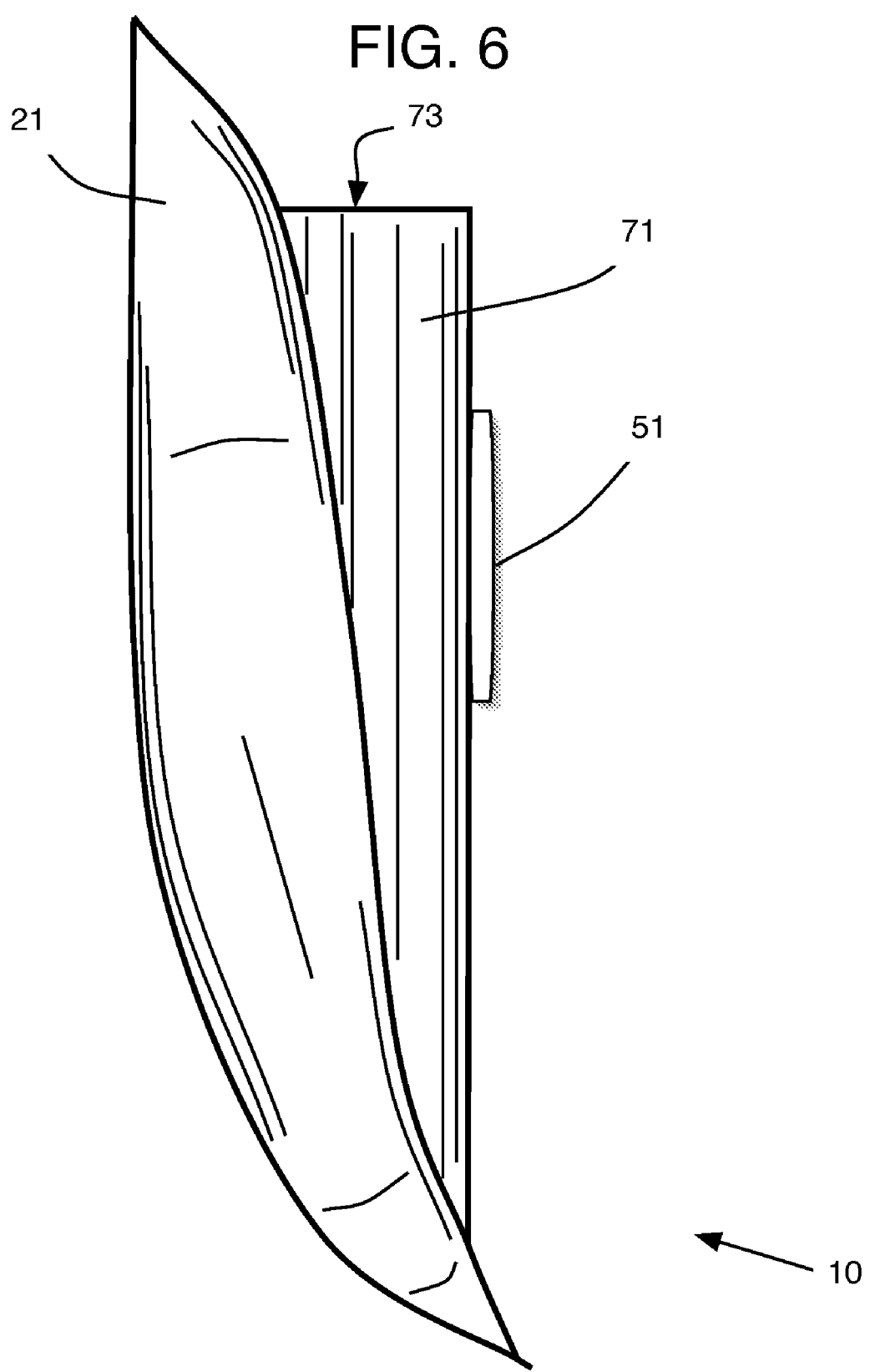
FIG. 6 is a right side view of a second embodiment of the present invention.

FIG. 6 shows another preferred embodiment of the present invention. An outer layer 21 and cooperating inner layer 31 (not shown in FIG. 6) sandwiches an inner cup 71 with an open top 73. A port 51 enables breast milk to flow into the compartment of the cup 71.

FIGS. 8-19 illustrate a second preferred embodiment of the present invention. The system 101 according to this preferred embodiment comprises a combination contoured cover and milk-collection container. The system 101 is a flexible apparatus made to fit inside a snug bra or tank top to collect breast milk that leaks from the side not being nursed or pumped—milk that is otherwise wasted based on the teachings of the prior-art.

Figure 8:
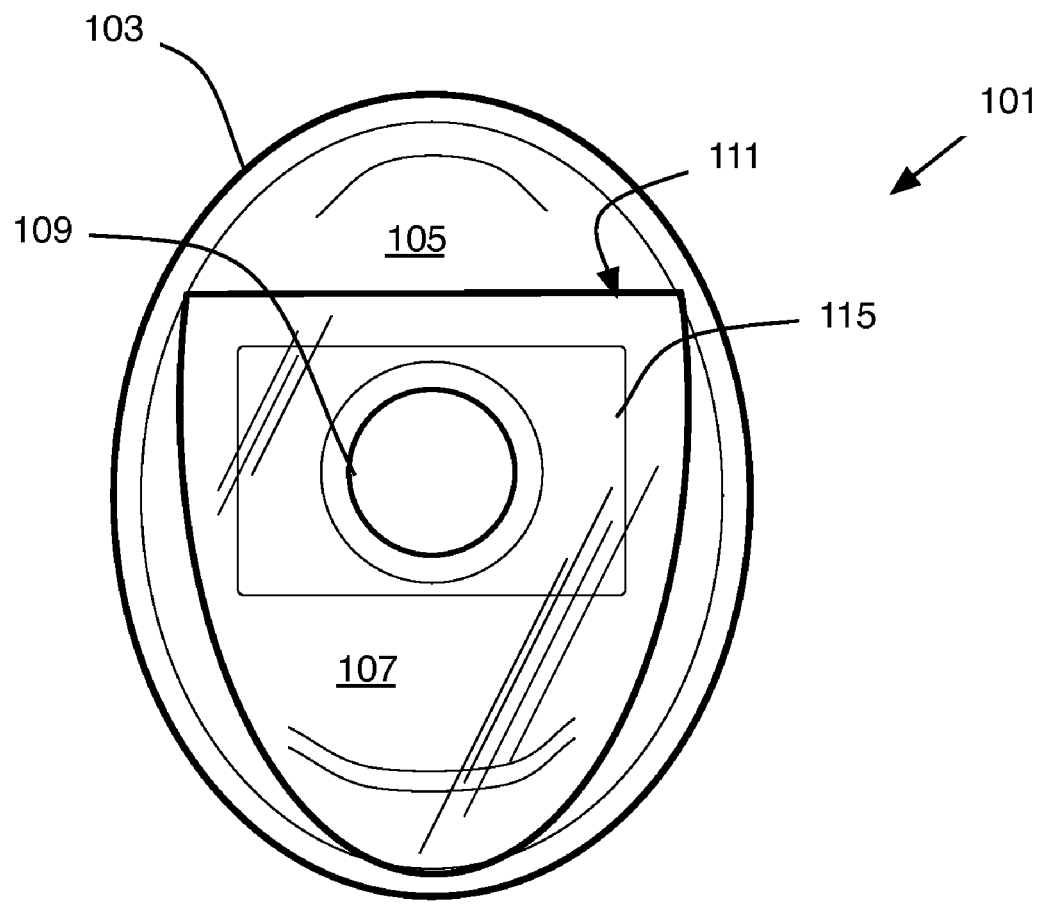
FIG. 8 is a back view of a second preferred embodiment of the present invention.

With particular reference to FIG. 8, the system 101 consists of a first member, a combination contoured cover and container 103. This combination device 103 includes a contoured cover having a first side (not shown in FIG. 8) adapted to fit completely under a single cup of a brassiere. This contoured member, presents a smooth surface on the first side, and the second side 105 emulates this shape and contour and provides a base to which at least one curvilinear retainer wall 107 couples. A top edge 111 of the at least one container wall 107 defines an open top portion, while the bottom edge forms a liquid impervious seam with the second side 105. A hole 109 disposed on the sidewall 109 is adapted to receive a nipple for the inflow of breast milk, opposite the first side.

Figure 14:
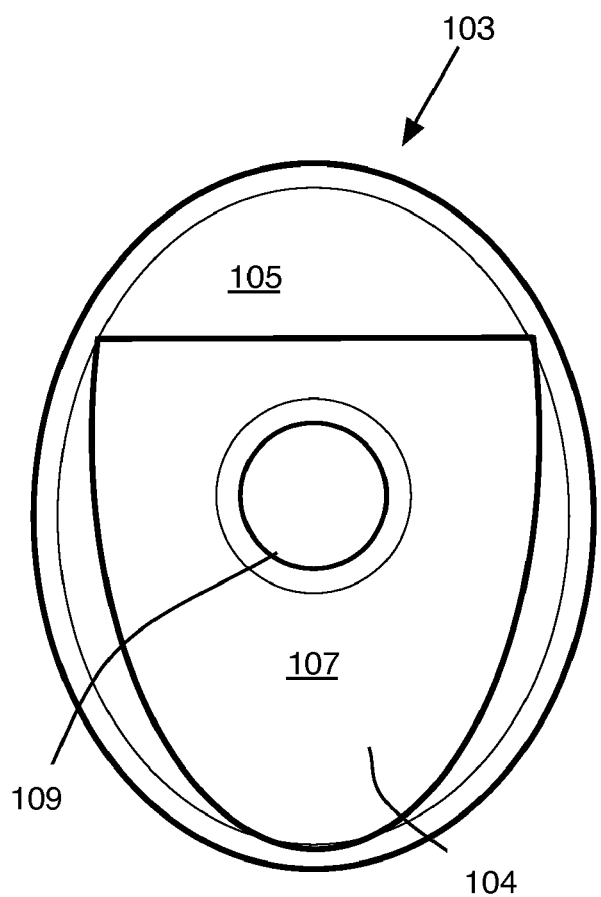
FIG. 14 is a back view of the combination container and contoured cover of the embodiment of FIG. 8.
Figure 15:
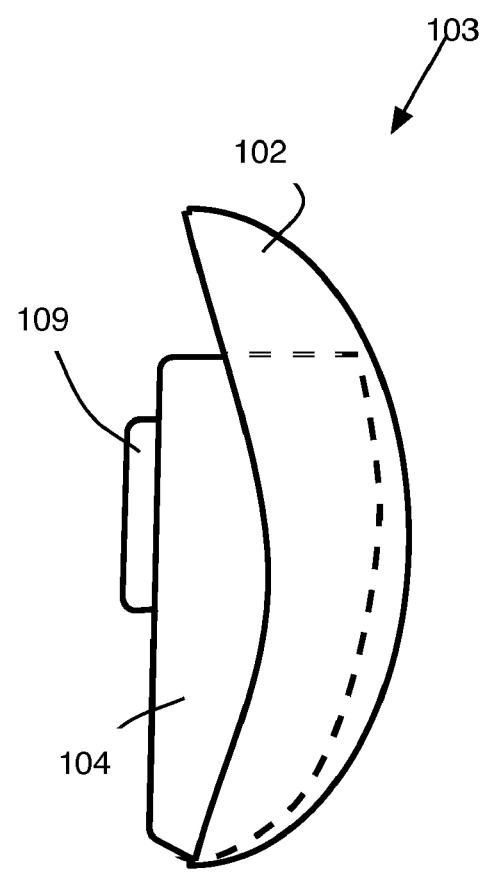
FIG. 15 is a left-side view of the combination container and contoured cover of FIG. 14.

FIGS. 14 and 15 illustrate the combination contour cover and container 103 of the breast milk collection and storage system 101. The contour cover and container 103 consists of an outer layer 102 having a first contour. The outer layer adapted to fit under a single cup of the brassier whereby the cup fully encases and encapsulates the outer layer, the outer layer having a first side consisting of a substantially smooth surface, the first side being arranged in contact with the cup, the outer layer further having a second side 105 opposite the first side, the second side forming one wall of a liquid-retaining cavity.

The contour cover and container 103 further includes an inner layer 104 having a second contour, the second contour emulating the contour of the female breast, the inner layer coupled to the outer layer thus defining the liquid retaining cavity, the inner layer further including at least one sidewall 107 coupled along at least one edge to the second side of the outer layer, at least a portion of the side wall forming an open top. The at least one sidewall 107 further including a nipple-receiving opening 109 creating a fluid conduit from the inner layer to the cavity, the cavity only having the nipple receiving opening as the only fluid path from and to the cavity for collection. Inverting the entire combination contour cover and container 103 empties the cavity. That is to say, there are no fluid conduits, pump mechanism or other devices used to draw milk from the breast or transfer milk from the small cavity that is fully encapsulated under the cup of the brassier on the single, non-nursing side during breastfeeding.

Figure 18:
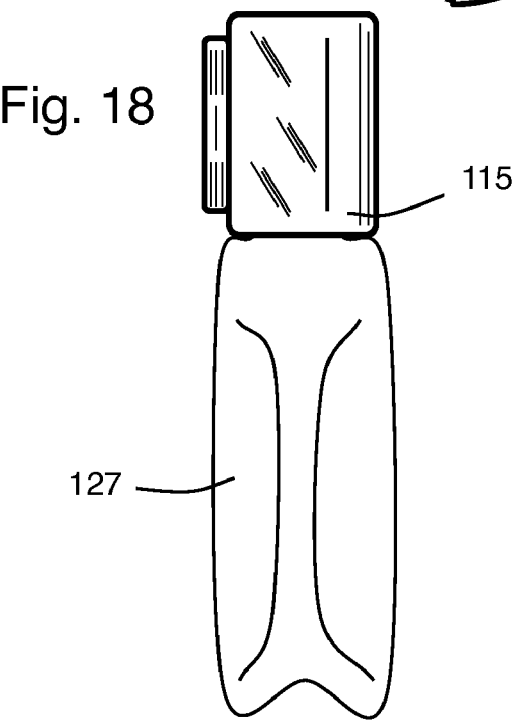
FIG. 18 shows the removal of the rim member relative to the combination contoured cover and container and further shows yet another step in a method of use, and further shows a storage bag coupled to the rim member, the rim member is inverted in this figure to the top of the rim member is adjacent to the bottom of the sheet.

FIGS. 9-13 illustrate a selectively removable rim device 115. The rim device inserts in the void defined between surface 105 and the at least one sidewall 107. The selectively removable rim device 115 consists of at least one sidewall 121 that arranges 360-degrees around to form a void with an open top and open bottom. Preferably, the rim device 115 includes a front sidewall 119 and second, curvilinear sidewall 121 to form an open top at the top edge 125 and an open bottom at the bottom edge 123. The front sidewall 119 further includes an insert edge hole feature 117, the insert edge adapted to selectively secure to the nipple-receiving hole 109 on the sidewall of the inner layer 107. This rim device serves as a spacer to offset the contoured cover piece from the container wall 107 so that the nipple is not constricted, and this further adds comfort to the wearer. Further, the rim device 115 easily adapts to secure a standard bottle liner (as FIG. 18 illustrates, for example).

Figure 19:
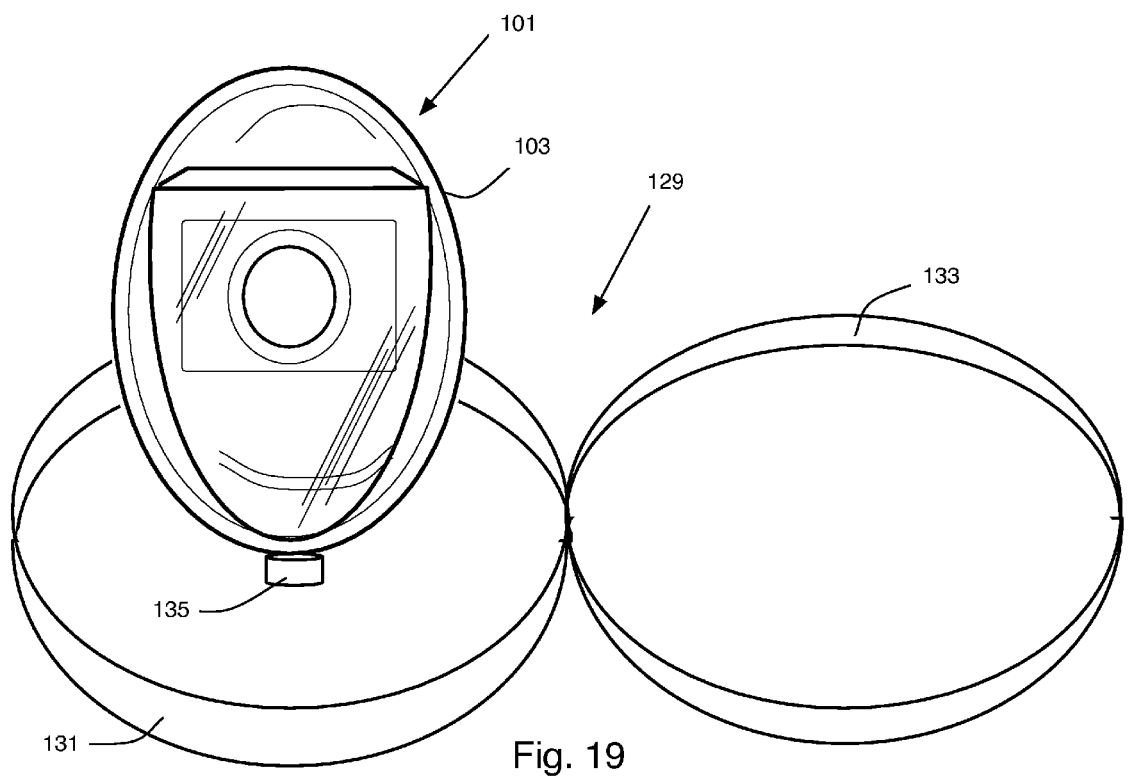
FIG. 19 is a front view of a holder device according to another embodiment of the present invention.

FIG. 19 illustrates a holder 129 for the system 101 and device 103 of the present invention. The holder 129 includes a cover 133 and base 131. The base includes a support 135 adapted to hold the combination cover and container 103 in an upright position. The cover closes over the base to form a vessel suitable for storing and transporting the combination container 103.

Method of Use

A method of use of any of the preferred embodiments of the device or apparatus of the present invention includes use during breastfeeding on the non-nursing breast. Accordingly, a system, such as system 101, is inserted under one cup of a nursing or other brassiere and arranged so the breast-feeding mom's nipple extends through the appropriate opening 109 on the container sidewall 111. An optional removable rim device 115 may be inserted in the container area between the container wall 107 and backside of the contour cover 105. The rim device 115 includes a hole edge insert feature 117, which is adapted to snugly fit on the inner diameter of the nipple-receiving hole 109.

Figure 16:
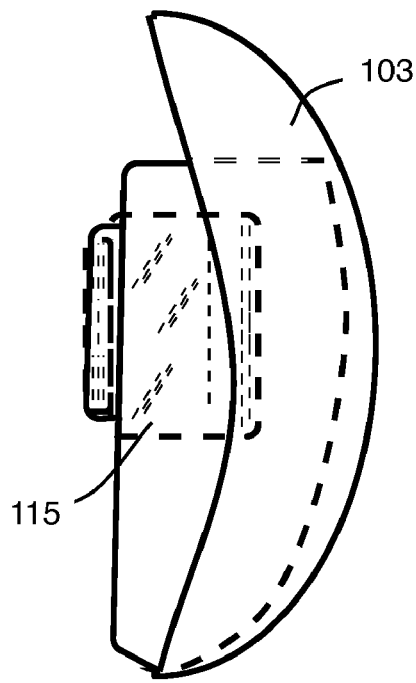
FIG. 16 is a left-side view of the embodiment of FIG. 8 illustrating a step in a method of use.

The entire system 101 fits under a single cup of a brassiere. Thus, during nursing on one breast, the system 101 arranges over the nipple of the second, non-nursing breast. As the system fits securely between the breast and the cup of the brassiere, the nursing mom is free to use both hands to nurse and hold the infant and/or massage the breasts to initiate lactation. Any milk that leaks from the non-nursing breast is then captured by the system 101 in the void between the cover and the container wall. This method utilizes the system 101 in the normal, upright orientation, as illustrated in FIG. 16. The leak-down milk is captured and subsequently transferred into a sterile storage device such as a bottle liner bag, or other hygienic and clean container such as a zip-lock-type bag. The milk is then refrigerated or frozen for future use.

Figure 17:
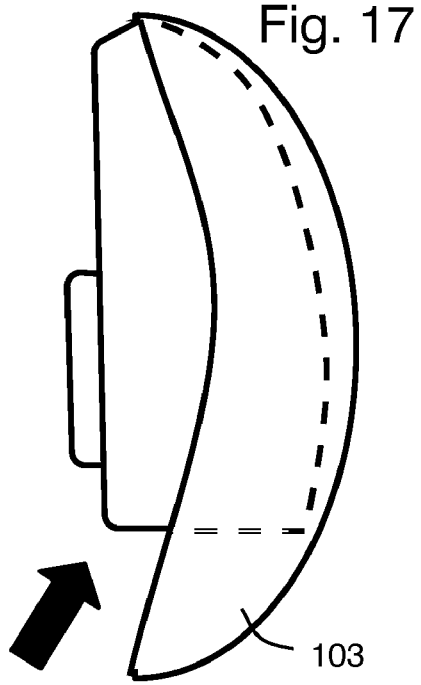
FIG. 17 shows the embodiment of FIG. 16 inverted top to bottom and illustrates another step in a method of use.

FIGS. 17 and 18 illustrate another optional sequence of steps of this preferred method of use. In this iteration, the system 101 including combination contour cover and container 103 is used in an inverted (upside down) position. A storage bag 127, such as a bottle liner attaches to the removable rim device 115 and bag, as an assembly, is inserted in the container compartment. This allows a larger leak-down volume to be captured during breastfeeding.

From these preferred embodiments of the device and method, it can be appreciated that the present invention vastly improves over the current teaching in the art. The present invention enables a nursing mom to capture leak-down milk—milk that would otherwise be wasted—during breastfeeding. Further, the present invention requires no external storage devices, requires no external or internal pumping means, and further enables the free-flow, unrestricted, of milk from the non-nursing side.

Although the invention has been particularly shown and described with reference to certain embodiments, it will be understood by those skilled in the art that various changes in form and detail may be made without departing from the spirit and scope of the invention.

We claim:

1. A breast milk collection and storage device adapted to fit over a human female nipple an portion of a female breast and adapted to be entirely encapsulated under a brassiere, the device comprising:

an outer layer comprising a contoured cover having a first side adapted to fit completely under a single cup of the brassiere and having a smooth surface on the first side, and further comprising a second side adapted to provide a base to which at least one curvilinear retainer wall couples, a top edge of the at least one container wall defines an open top portion, while the bottom edge forms a liquid impervious seam with the second side, the outer layer further comprising a convex elliptical form when viewed from above and measuring about a 6-inch diameter on the minor axis and about an 8-inch diameter on the major axis and consists of a relatively soft and resiliently deformable material material;

the second side further comprising an inner layer having a second contour, the second contour emulating the contour of the female breast, the inner layer coupled to the outer layer thus defining the liquid retaining cavity, a nipple-receiving opening disposed on the second side adapted to create a fluid conduit from the inner layer to the liquid retaining cavity;

a retaining means disposed between the inner layer and outer layer and a portion of the retaining means arranged around the nipple-receiving opening and the retaining means adapted to receive fluid; and the retaining means further comprising a selectively removable rim device comprising at least one sidewall arranged to form a void having an open bottom and an open top, the side wall further including an insert edge hole feature, the insert edge adapted to selectively secure to the nipple-receiving hole on the sidewall of the inner layer.

2. The device of claim 1 further comprising:

the retaining means comprises an inner cup container adapted to receive breast milk;

the cup container having at least one vertical sidewall, a bottom and an open top, the sidewall, bottom and top cooperating to form a compartment adapted to hold breast milk; and the vertical sidewall further comprising a port adapted to cooperate with the nipple-receiving opening whereby a fluid conduit is formed from the inner layer to the inner compartment of the cup container.

3. The breast milk collection and storage device of claim 1 wherein the retaining means further comprises a collection bag having a sealing means for closing the collection bag when removed from the cavity.

4. The breast milk collection and storage device of claim 1 wherein the retaining means further comprises an elastically deformable retention member.

5. A method of using a breast milk collection and storage device adapted to fit over a human female nipple an portion of a female breast and adapted to be entirely encapsulated under a brassiere, the method comprising:

providing a collection device comprising an outer layer comprising a contoured cover having a first side adapted to fit completely under a single cup of the brassiere and having a smooth surface on the first side, and further comprising a second side adapted to provide a base to which at least one curvilinear retainer wall couples, a top edge of the at least one container wall defines an open top portion, while the bottom edge forms a liquid impervious seam with the second side, the outer layer further comprising a convex elliptical form when viewed from above and measuring about a 6-inch diameter on the minor axis and about an 8-inch diameter on the major axis and consists of a relatively soft and resiliently deformable material material;

the second side further comprising an inner layer having a second contour, the second contour emulating the contour of the female breast, the inner layer coupled to the outer layer thus defining the liquid retaining cavity, a nipple-receiving opening disposed on the second side adapted to create a fluid conduit from the inner layer to the liquid retaining cavity;

a retaining means disposed between the inner layer and outer layer and a portion of the retaining means arranged around the nipple-receiving opening and the retaining means adapted to receive fluid; and the retaining means further comprising a selectively removable rim device comprising at least one sidewall arranged to form a void having an open bottom and an open top, the side wall further including an insert edge hole feature, the insert edge adapted to selectively secure to the nipple-receiving hole on the sidewall of the inner layer;

inserting the collection device under a cup of the brassiere and aligning the opening over a non-breast-feeding breast during breast-feeding.

* * * * *